US010195367B2

(12) United States Patent
Schmidt et al.

(10) Patent No.: US 10,195,367 B2
(45) Date of Patent: Feb. 5, 2019

(54) MEDICAL WETNESS SENSING DEVICES AND RELATED SYSTEMS AND METHODS

(71) Applicant: Fresenius Medical Care Holdings, Inc., Waltham, MA (US)

(72) Inventors: Daniel Schmidt, Petaluma, CA (US); Elliott Alber, Pleasanton, CA (US); Colin Weaver, Pleasanton, CA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 454 days.

(21) Appl. No.: 14/886,427

(22) Filed: Oct. 19, 2015

(65) Prior Publication Data

US 2017/0106151 A1    Apr. 20, 2017

(51) Int. Cl.
*A61M 31/00* (2006.01)
*A61M 37/00* (2006.01)
(Continued)

(52) U.S. Cl.
CPC ....... *A61M 5/5086* (2013.01); *A61B 5/02042* (2013.01); *A61F 13/00055* (2013.01);
(Continued)

(58) Field of Classification Search
CPC .......... A61M 2205/15; A61M 2205/18; A61M 2205/3584; A61M 5/5086; A61M 1/3656;
(Continued)

(56) References Cited

U.S. PATENT DOCUMENTS 7,147,615 B2    12/2006    Wariar et al.
7,605,710 B2 *  10/2009    Crnkovich .............. A61F 13/42
                                                   340/603
(Continued)

FOREIGN PATENT DOCUMENTS

CN    104769423    7/2015
WO    1999026686   6/1999

OTHER PUBLICATIONS

International Search Report and Written Opinion in International Application No. PCT/US2016/056743, dated Feb. 22, 2018, 11 pages.

(Continued)

*Primary Examiner* — Jason Flick
(74) *Attorney, Agent, or Firm* — Fish & Richardson P.C.

(57) ABSTRACT

A medical wetness sensing device includes a cover, a first and second electrically conductive portions housed in the cover, an electrically insulative portion housed in the cover, and a compressible portion. The cover defines an outer surface. The first and second electrically conductive portions are exposed along an inner surface of the medical wetness sensing device. The first and second electrically conductive portions are configured to transmit a test signal indicating an absence or presence of a liquid on the inner surface. The electrically insulative portion electrically isolates the first electrically conductive portion from the second electrically conductive portion. The compressible portion is flexible, compressible, and configured such that the inner surface of the medical wetness sensing device is conformable to skin of a wearer of the medical wetness sensing device The compressible portion is formed by at least one of the cover, the first and second electrically conductive portions, and the electrically insulative portion.

31 Claims, 7 Drawing Sheets

(51) Int. Cl.

| | |
|---|---|
| *A61F 13/15* | (2006.01) |
| *A61F 13/20* | (2006.01) |
| *A61M 5/50* | (2006.01) |
| *A61M 5/168* | (2006.01) |
| *A61B 5/02* | (2006.01) |
| *A61M 1/36* | (2006.01) |
| *A61F 13/00* | (2006.01) |

(52) U.S. Cl.
CPC ...... *A61M 1/3656* (2014.02); *A61M 5/16836* (2013.01); *A61F 2013/00412* (2013.01); *A61M 2205/15* (2013.01); *A61M 2205/18* (2013.01); *A61M 2205/3317* (2013.01); *A61M 2205/3569* (2013.01); *A61M 2205/3584* (2013.01); *A61M 2205/3592* (2013.01)

(58) Field of Classification Search
CPC .. A61M 2205/3317; A61M 2205/3569; A61M 2205/3592; A61M 5/16836; A61F 13/00055; A61F 2013/00412; G01N 27/121; G08B 21/20
USPC .......................................................... 604/506
See application file for complete search history.

(56) References Cited

U.S. PATENT DOCUMENTS

| | | | |
|---|---|---|---|
| 7,973,667 | B2 | 7/2011 | Crnkovich et al. |
| 8,981,948 | B2 | 3/2015 | Olde et al. |
| 2008/0252447 | A1* | 10/2008 | Atherton ................ G08B 17/10 340/540 |
| 2013/0053754 | A1 | 2/2013 | Heppe |
| 2014/0012197 | A1 | 1/2014 | Heppe et al. |
| 2014/0106151 | A1 | 4/2014 | Mori |
| 2014/0183106 | A1 | 7/2014 | Kotsos et al. |
| 2014/0350503 | A1* | 11/2014 | Bosaeus ................. A61F 13/42 604/361 |

OTHER PUBLICATIONS

"Patient Safety by Fresenius Medical Care; Where new benchmarks are set," Cardioprotective Haemodialysis, Fresenius Medical Care Deutschland GmbH, 2012, 20 pages.

International Preliminary Report on Patentability in International Application No. PCT/US2016/056743, dated Apr. 24, 2018, 9 pages.

* cited by examiner

MEDICAL WETNESS SENSING DEVICES AND RELATED SYSTEMS AND METHODS

TECHNICAL FIELD

This disclosure relates to systems and devices for sensing wetness, in particular, to systems and devices for sensing wetness during a hemodialysis treatment.

BACKGROUND

During hemodialysis treatment, a venous access needle may become dislodged. In the case that such an event goes unnoticed, an arterial access needle can continue to draw blood from the patient while the dislodged venous access needle does not return blood to the patient.

SUMMARY

A medical wetness sensing device can be placed on the skin of a patient during treatment to detect an absence or presence of liquid along a surface of the medical wetness sensing device facing the skin. The medical wetness sensing device can be placed above a venous access site where a venous needle punctures the skin of the patient to access a circulatory system of the patient. The liquid can be blood that leaks from the patient through the venous access site. When the medical wetness sensing device is placed above the venous access site, additional pressure can be applied to the medical wetness sensing device to ensure contact between blood and the wetness sensing device during a blood leak.

The medical wetness sensing device can be flexible and compressible. In this regard, when the medical wetness sensing device is applied to the skin of the patient, the flexibility of the medical wetness sensing device allows the wetness sensing device to bend about contours of the skin of the patient. The compressibility of the wetness sensing device allows the wetness sensing device to conform to the skin and any other items underlying the wetness sensing device, such as the venous needle used to puncture the skin. The elasticity of the wetness sensing device can be similar to that of the skin or greater than the elasticity of skin.

In one aspect a medical wetness sensing device includes a cover, a first and second electrically conductive portions housed in the cover, an electrically insulative portion housed in the cover, and a compressible portion. The cover defines an outer surface. The first and second electrically conductive portions are exposed along an inner surface of the medical wetness sensing device. The first and second electrically conductive portions are configured to transmit a test signal indicating an absence or presence of a liquid on the inner surface. The electrically insulative portion electrically isolates the first electrically conductive portion from the second electrically conductive portion. The compressible portion is flexible, compressible, and configured such that the inner surface of the medical wetness sensing device is conformable to skin of a wearer of the medical wetness sensing device. The compressible portion is formed by at least one of the cover, the first and second electrically conductive portions, and the electrically insulative portion.

In some examples, the compressible portion comprises a foam elastomer. The foam elastomer can have a density between 0.3 grams per cubic centimeter and 5 grams per cubic centimeter. The insulative portion can include the foam elastomer and can at least partially form the compressible portion. The first and second conductive portions can include a conductive mesh disposed along the foam elastomer. The medical wetness sensing device can further include a sheet of cloth forming the inner surface of the medical wetness sensing device and a conductive mesh woven through the sheet of cloth such that the conductive mesh is exposed along the inner surface. The conductive mesh can form at least one of the first and second electrically conductive portions.

In some examples, the compressible portion includes a dense elastomer.

In some examples, the compressible portion includes a compressible tube.

In some examples, the first and the second conductive portions are disposed along a surface of the insulative portion. The first and the second conductive portions can include a conductive ink deposited on the surface of the insulative portion.

In some examples, the first and second electrically conductive portions define a gap between the first and second electrically conductive portions. The gap can be filled, in part, by the electrically insulative portion. The gap can have a width between 0.5 and 4 millimeters.

In some examples, the electrically conductive portions can include at least one of black carbon, graphene flakes, carbon nanotubes, silver, copper, stainless steel mesh, and nickel.

In some examples, the compressible portion is formed by at least the first and second electrically conductive portions.

In some examples, in the presence of the liquid, the test signal transmitted by the first and second electrically conductive portions indicates electrical continuity between the first electrically conductive portion and the second electrically conductive portion.

In some examples, the medical wetness sensing device further includes a power source housed in the cover embedded beneath the outer surface of the medical wetness sensing device.

In some examples, the medical wetness sensing device further includes a wireless transmitter embedded beneath the outer surface of the medical wetness sensing device.

In another aspect, a hemodialysis system includes a hemodialysis machine including a wireless receiver and a medical wetness sensing device configured to generate a signal indicating presence of a liquid on an inner surface of the medical wetness sensing device. The medical wetness sensing device includes a cover, a compressible portion, and a wireless transmitter housed in the cover. The compressible portion is flexible, compressible, and configured such that the inner surface of the medical wetness sensing device is conformable to skin of a wearer of the medical wetness sensing device. The wireless transmitter is configured to transmit the signal to the wireless receiver of the hemodialysis machine.

In some examples, the medical wetness sensing device further includes an electrically insulative portion and first and second electrically conductive portions housed in the cover and exposed along the inner surface of the medical wetness sensing device. The first and second electrically conductive portions can be configured to transmit a test signal indicating an absence or the presence of the liquid on the inner surface. The compressible portion can be formed by at least one of the cover, the electrically insulative portion, and the first and second electrically conductive portions.

In some examples, in the presence of the liquid, the test signal transmitted by the electrically conductive portions indicates electrical continuity between the first electrically conductive portion and the second electrically conductive portion.

In some examples, the first and second electrically conductive portions define a gap therebetween. The gap can be filled, in part, by the electrically insulative portion.

In a further aspect, a method includes puncturing, using a needle, an access site on skin of a patient to access a corporeal blood circuit of the patient and placing a medical wetness sensing device over the skin surrounding the access site such that an inner surface of the medical wetness sensing device faces the skin. The medical wetness sensing device includes a compressible portion that is flexible, compressible, and configured such that the inner surface of the medical wetness sensing device is conformable to the skin.

In some examples, the medical wetness sensing device includes a cover defining an outer surface, first and second electrically conductive portions housed in the cover, and an electrically insulative portion housed in the cover. The first and second electrically conductive portions can be exposed along an inner surface of the medical wetness sensing device. The first and second electrically conductive portions can be configured to generate a signal indicating an absence or presence of a liquid on the inner surface. The electrically insulative portion electrically can isolate the first electrically conductive portion from the second electrically conductive portion. The compressible portion can be formed by at least one of the cover, the first and second electrically conductive portions, and the electrically insulative portion.

In some examples, the method further includes securing the medical wetness sensing device to the skin with an adhesive.

In some examples, the method further includes securing the medical wetness sensing device to the skin with cloth wrapped around an arm of the patient.

In some examples, the method further includes initiating a hemodialysis treatment on a hemodialysis machine configured to receive a signal from the medical wetness sensing device. The signal can indicate an absence or presence of a liquid on an inner surface of the medical wetness sensing device.

In some examples, placing the medical wetness sensing device in direct contact with the skin surrounding the needle further can include placing the medical wetness sensing device in direct fluid communication with liquid that leaks from the access site.

Advantages of the foregoing may include, but are not limited to one or more, of the following. The flexibility and the compressibility of the wetness sensing device allow the wetness sensing device to conform to underlying geometries of the skin of the patient, the venous needle, and the blood lines, without applying excessive pressure that can cause discomfort for the patient. The wetness sensing device, by conforming to the skin and medical instruments, maintains a greater amount of contact with the skin, particularly around the access site for the venous needle. As a result, the wetness sensing device contacts any blood that leaks from the venous access site, enabling the wetness sensing device to generate signals in response to contact the blood.

The wetness sensing device is more comfortable for the patient. Upon applying the wetness sensing device to the skin, the pressure used to apply the wetness sensing device to the skin can cause compression of the wetness sensing device. The compression of the wetness sensing device reduces movement of the skin and the venous needle, which can cause the patient to experience pain and discomfort.

The details of one or more implementations are set forth in the accompanying drawings and the description below. Other features and advantages will be apparent from the description and drawings, and from the claims.

DETAILED DESCRIPTION

Access to a circulatory system of the patient may require puncturing the skin of a patient using a needle, a catheter, or other sharp device to form an access. Procedures that can require access to the circulatory system can include hemodialysis, blood filtration, hemofiltration, blood donation, blood detoxification, apheresis, cardiac catheterizations, among other blood treatment procedures. During a hemodialysis treatment using a hemodialysis machine, the needle can place the circulatory system in fluid communication with an extracorporeal system. Blood circulates through the extracorporeal system and undergoes filtering within the extracorporeal system. In some cases, blood from the patient can leak through the access site onto the skin of the patient. The needle can dislodge from the access site during treatment due to movement of the patient or inadvertent contact with the needle. The dislodged needle can lead to patient blood loss. A wetness sensing device placed on the needle and over the access site can detect the blood leaking from the access site so that the patient or an operator of the hemodialysis machine can resolve the leak, stop the treatment, or otherwise change the course of treatment in response to the leak. The wetness sensing device can be flexible, compressible, and conformable to the skin of the patient so that the wetness sensing device can conform to the skin and contact blood leakages that can occur during the extracorporeal treatment. The flexibility and compressibility enable the wetness sensing device to be pressed against the skin and wrapped around contours of the patient's body while maintaining close contact with the skin so that blood leakages are quickly and reliably detected.

Overview of System

Figure 1A:
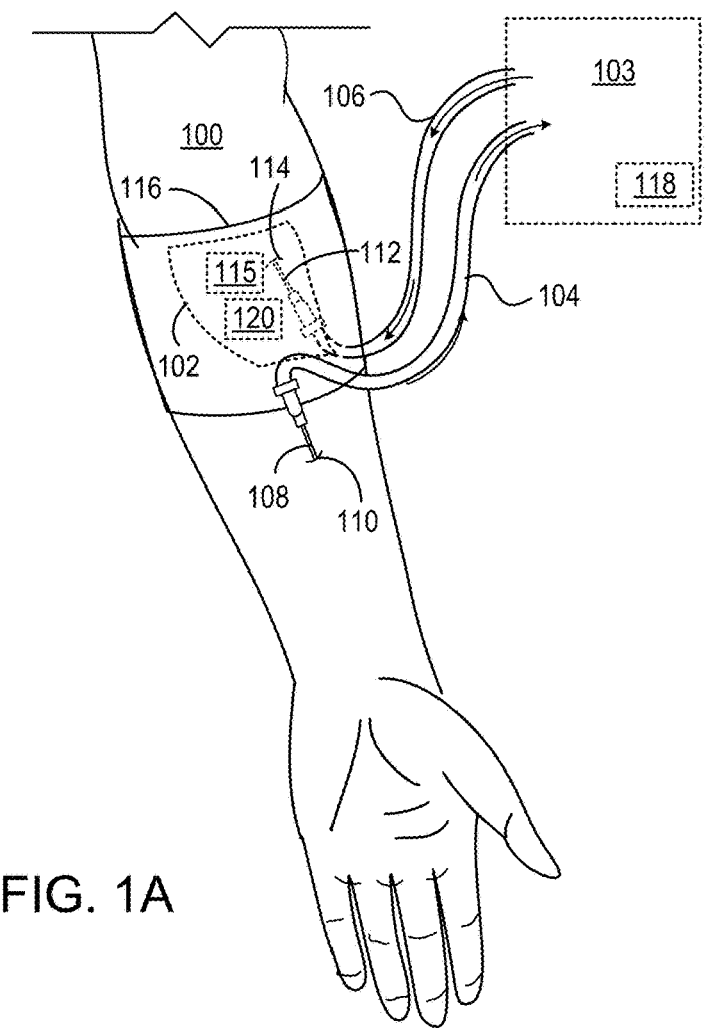
FIG. 1A illustrates an access in an arm of a patient undergoing extracorporeal treatment of blood.

FIG. 1A illustrates a medical wetness sensing device 102 in use on a patient 100 undergoing an extracorporeal treatment (e.g., a dialysis treatment) in which blood from the patient 100 is circulated from the circulatory system of the patient through an extracorporeal system (e.g., a dialysis system) 103. An arterial line 104 moves the blood from the patient 100 to the extracorporeal system 103. The extracorporeal system 103 then returns the blood through a venous line 106 that moves the blood back to the circulatory system of the patient 100. An arterial needle 108 inserted into an arterial access site 110 of the patient 100 places the circulatory system of the patient 100 in fluid communication with the arterial line 104 and thus the extracorporeal system 103. Similarly, a venous needle 112 inserted into a venous access site 114 places the circulatory system of the patient in fluid communication with the venous line 106 and thus the extracorporeal system 103. The arterial needle 108 and the venous needle 112 are typically inserted into a forearm of the patient 100.

Figure 1B:
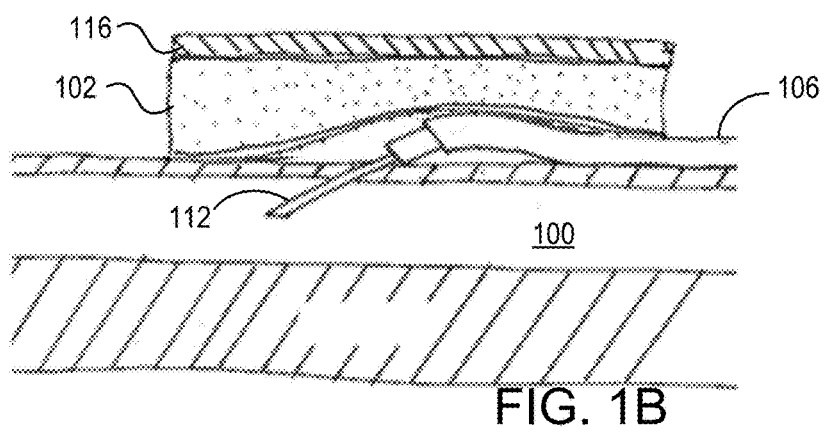
FIG. 1B is a schematic cross-sectional side view of a wetness sensing device used in the extracorporeal treatment of blood shown in FIG. 1A.

As shown in FIG. 1B, a wetness sensing device 102 is flexible and compressible, thereby allowing the wetness sensing device 102 to conform to the skin and to the venous needle 112. In particular, an inner surface of the wetness sensing device 102 (e.g., a surface of the wetness sensing device 102 facing the venous access site 114) conforms to the skin. The geometry of the inner surface, because of the compressibility and flexibility properties of the wetness sensing device 102, can closely match the geometry of the venous access site. The wetness sensing device 102 can be compressed to achieve curvatures that a less compressible wetness sensing device would be unable to achieve.

The inner surface of the wetness sensing device 102 can be pressed against the skin of the patient to conform to the contours of the skin (e.g., contours of the patient's forearm). The inner surface of the wetness sensing device 102 can be compressed against the skin so that a greater amount of the inner surface of the wetness sensing device 102 facing the skin of the patient maintains direct or indirect contact as compared to the amount of surface contact of a less compressible wetness sensing device. In addition, the compressibility of wetness sensing device 102 allows the inner surface of the wetness sensing device 102 to conform around sharp or abrupt changes in geometries underlying the wetness sensing device 102 caused by, for example, the venous needle 112. In some cases, the wetness sensing device 102 can have elastic properties similar to the skin of the patient 100.

During use, after the wetness sensing device 102 is applied to the skin of the patient 100 and over the venous needle 112, a cloth 116 is wrapped around the wetness sensing device 102 to the fix wetness sensing device 102 in place. The cloth 116 generates a pressure on top of the wetness sensing device 102, causing the wetness sensing device 102 to compress against the skin of the patient 100 and the venous needle 112. Because the wetness sensing device 102 is compressed against the skin and is compressible, the inner surface of the wetness sensing device 102 easily conforms to the curvature of the skin of the patient 100. The process of applying and securing the wetness sensing device 102 in place is less likely to result in excessive pressure on the venous needle 112 and impingement of the skin, which can cause pain or discomfort for the patient 100. The flexibility and compressibility of the wetness sensing device 102 reduce skin impingement and excessive pressure.

The wetness sensing device 102, when applied and secured against the skin, also maintains better contact with the skin of the patient and the venous needle 112 so that the wetness sensing device 102 can more quickly detect blood leaks from the venous needle 112. By conforming to the skin, the inner surface of the wetness sensing device 102 can also be placed in closer contact to blood leaks from the patient 100 to more easily detect the blood leaks. In some examples, the wetness sensing device 102 can be applied directly against the skin such that the inner surface of the wetness sensing device 102 contacts the skin.

The wetness sensing device 102, in response to detecting leakage of blood, can transmit wireless signals to alert external systems of the leak. The wetness sensing device 102 includes a wireless transceiver 115 that can communicate with a wireless transceiver 118 of the extracorporeal system 103. The wetness sensing device 102 further includes a power source 120 to supply power to the wireless transceiver 115 such that the wetness sensing device 102 does not require a wired power connection to an external power source.

The wetness sensing device 102 can detect absence or presence of a liquid (e.g., blood) on the inner surface of the wetness sensing device 102. Based on the detection, the operator or the extracorporeal system 103 can, for example, change a course of treatment to reduce risk to the patient 100. The wetness sensing device 102 can generate an electrical signal indicating an absence of presence of blood. The wireless transceiver 115 of the wetness sensing device 102 can receive the electrical signal and generate a wireless signal based on the electrical signal. The wireless transceiver 115 can transmit the wireless signals using a wireless communications technology, such as, Near Field Communication, Bluetooth, or WiFi. The wireless transceiver 118 can receive the wireless signal from the wireless transceiver 115 of the wetness sensing device. Based on the wireless signal, the wireless transceiver 118 can generate electrical signals that the extracorporeal system 103 can use to change the course of treatment.

If the wetness sensing device 102 does not detect blood, the wetness sensing device 102 can generate an electrical signal indicating the absence of blood. The extracorporeal system 103 receives the wireless signal indicating the absence of blood and, in response, can continue with treatment uninterrupted. In some cases, the wetness sensing device 102 can operate in an idle state in which it does not generate the electrical signal in the absence of blood.

In the event that a blood leak occurs due to, for example, dislodgement or disconnection of the venous needle 112, the wetness sensing device 102 can generate a wireless signal indicating the presence of blood. In response to the wireless signal indicating the presence of blood, the extracorporeal system 103 can stop the treatment, reduce a pump speed of a pump of the extracorporeal system 103, or otherwise change the treatment parameters to prevent additional blood leakage. Alternatively or additionally, the extracorporeal system 103 can display an error message or issue an alarm indicating to the operator that the blood leak has occurred. The operator can then resolve the blood leak by changing the treatment parameters or by adjusting components such as, for example, the venous needle 112 and the cloth 116.

Wetness Sensing Devices

Figure 2:
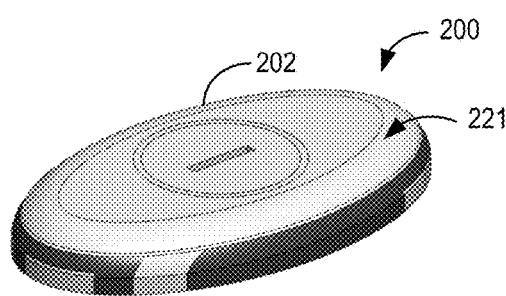
FIG. 2 is a top perspective view of an example of a wetness sensing device.
Figure 3:
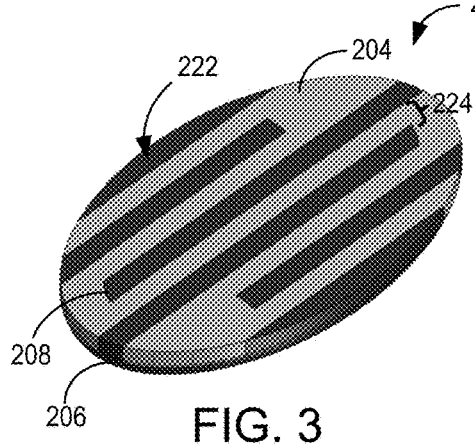
FIG. 3 is a bottom perspective view of the wetness sensing device of FIG. 2.
Figure 4:
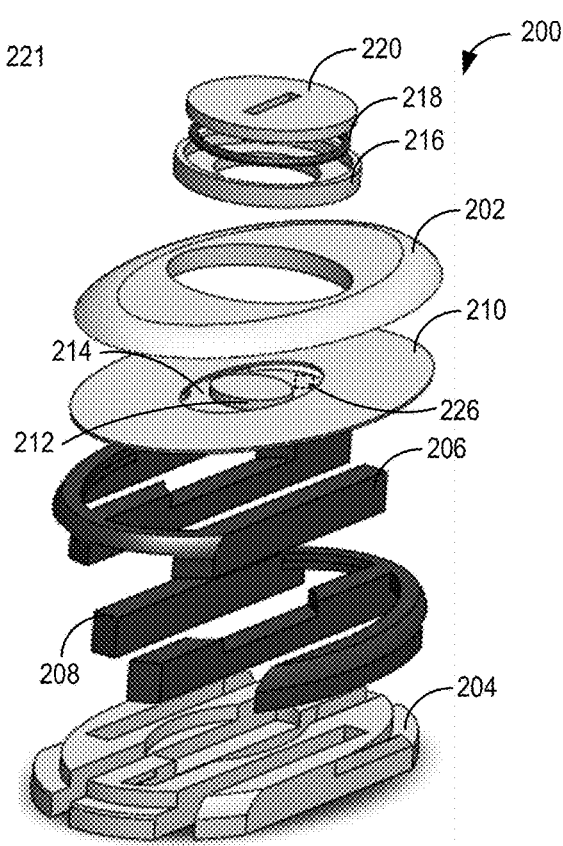
FIG. 4 is an exploded top perspective view of the wetness sensing device of FIG. 2.
Figure 7:
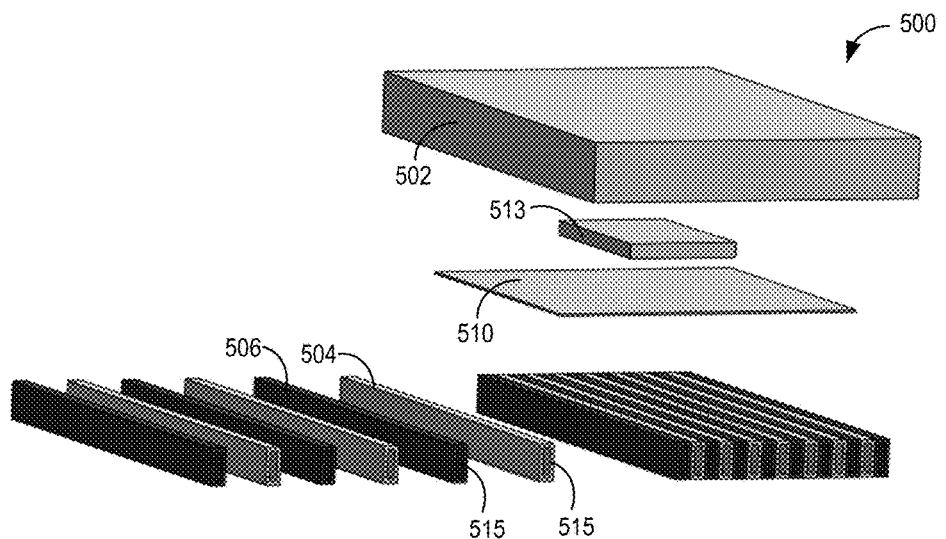
FIG. 7 is an exploded top perspective view of the wetness sensing device of FIG. 5.
Figure 8:
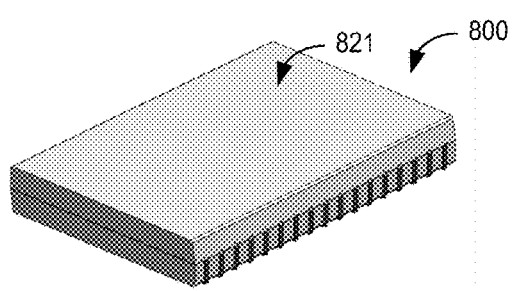
FIG. 8 is a top perspective view of another example of a wetness sensing device.
Figure 9A:
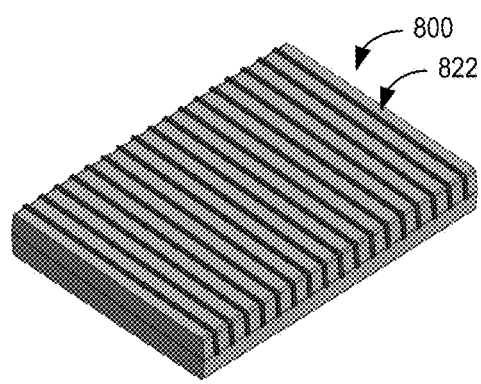
FIG. 9A is bottom perspective view of the wetness sensing device of FIG. 8.
Figure 9B:
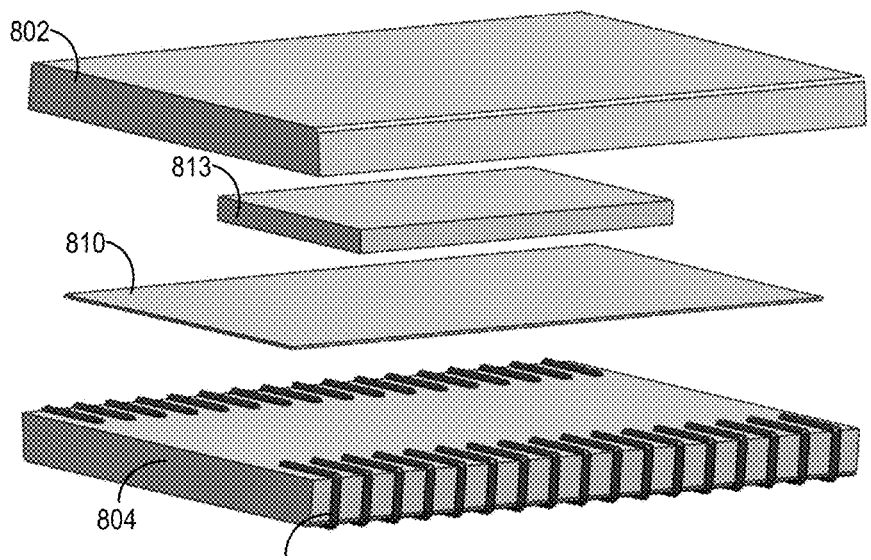
FIG. 9B is an exploded top perspective view of the wetness sensing device of FIG. 8.
Figure 10A:
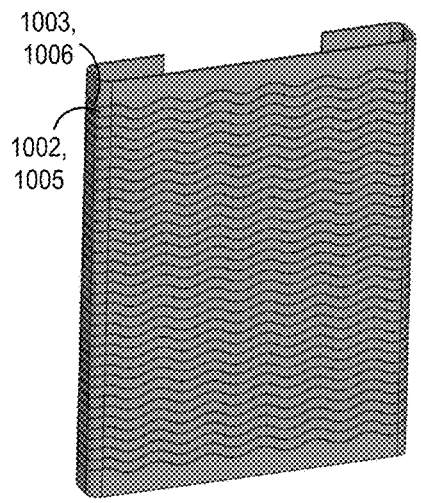
FIG. 10A is a bottom perspective view of a portion of a wetness sensing device.
Figure 10B:
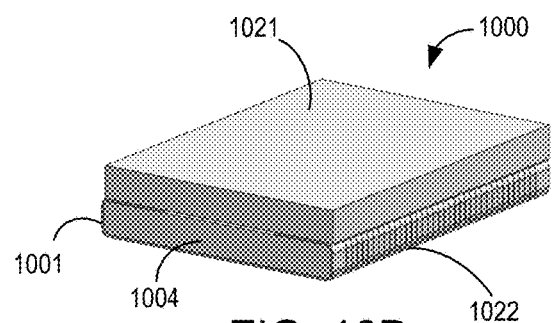
FIG. 10B is a top perspective view of the wetness sensing device of FIG. 10A.
Figure 10C:
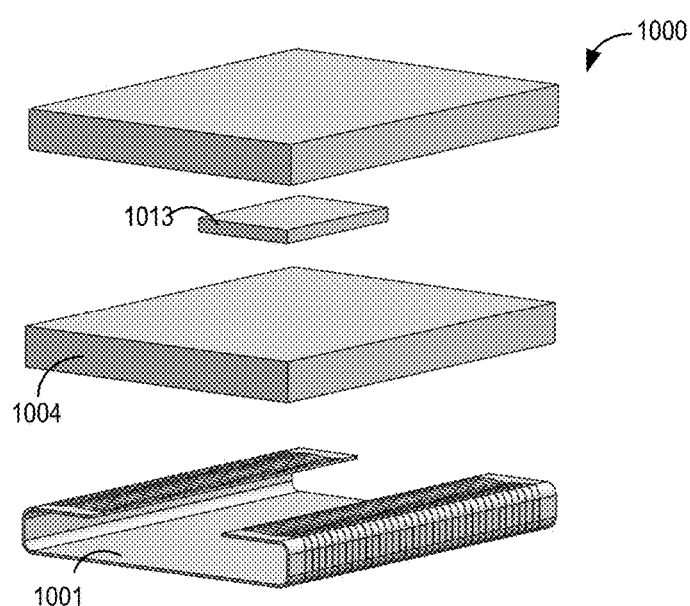
FIG. 10C is an exploded top perspective view of the wetness sensing device of FIG. 10A.

A compressible and flexible wetness sensing device (e.g., the wetness sensing device 102) that can detect blood leaks from a patient (e.g., the patient 100) can be implemented in a number of ways described herein. FIGS. 2 to 4 depict a first example, FIGS. 5 to 7 herein are merely examples and depict a second example, FIGS. 8, 9A, and 9B depict a third example, and FIGS. 10A to 10C depict a fourth example. The examples set forth herein are merely examples and do not limit the scope of this disclosure.

In the first example of the wetness sensing device, the wetness sensing device can include two separate interlocking conductive portions that form part of an electrically continuous path in the presence of blood. The interlocking conductive portion and insulative portions separating the conductive portions are made of foam material that allow the wetness sensing device to be compressible and thus conformable to skin of a wearer of the wetness sensing device as well as abrupt changes in geometries along the skin caused by, for example, an inserted venous needle. FIGS. 2 to 4, depicting the first example of the wetness sensing device, show a wetness sensing device 200 that includes a cover 202, an insulative portion 204, and first and second conductive portions 206, 208. The cover 202 houses and supports the insulative portion 204, the first conductive portion 206, the second conductive portion 208, a contact pad 210, a printed circuit board 212, a power source 214, a power source housing 216, a power source seal 218, and a power source cover 220.

The cover 202 and the power source cover 220 define, in part, an outer surface 221 (e.g., a surface facing away from skin of a wearer of the wetness sensing device 200) that is generally not exposed to blood leaking from a wearer of the wetness sensing device 200. The cover 202 and the power source cover 220 can prevent damage due to, for example, liquid infiltrating into internal components, such as the printed circuit board 212 and the power source 214.

The power source 214 is removably housed in the power source housing 216. The power source cover 220 is removably placed on the power source housing 216 and seals the power source 214 from an outside environment such that blood and other liquids cannot enter the power source housing 216 and damage the power source 214 or the printed circuit board 212. When the power source cover 220 is removed from the power source housing 216, the power source 214 can be removed and inserted. As a result, the power source 214 can be replaceable in an event that the power source 214 does not have sufficient power to energize the printed circuit board 212.

The wetness sensing device 200 includes a compressible and flexible portion that can experience large deformations in response to compression, thus allowing the wetness sensing device 200 to conform to the skin of the wearer. When an inner surface 222 (e.g., a surface of the wetness sensing device 200 that faces skin of a wearer of the wetness sensing device 200) is placed and pressed against the skin of the patient, the compressible and flexible portion of the wetness sensing device 200 deforms to conform to the skin and the venous needle. The compressible and flexible portion allows the wetness sensing device 200 to deform such that the inner surface 222, despite uneven and sharp geometries that the combination of the wearer's skin and the venous needle generate, maintains contact with the skin of the wearer.

As a consequence of these deformations to conform to and curve around the skin, the compressible and flexible portion experiences compressive stresses and strains. The inner surface 222 of the wetness sensing device 200 is, for example, placed on top of a venous needle (e.g., the venous needle 112) and the wearer's forearm, both of which include curved geometry to which the inner surface 222 conforms. The compressible and flexible portion of the wetness sensing device 200 experiences strains based on the amount of bending that occurs as it conforms about the venous needle and the wearer's forearm. The material and construction of the wetness sensing device 200 enable the compressible and flexible portion to elastically deform so that the wetness sensing device 200 can achieve curvatures that render the inner surface 222 conformable to the wearer's forearm. The wetness sensing device 200, while it is conforming to the venous needle and the wearer's forearm, maintains its functionality to sense wetness and blood. In particular, the compressible and flexible portion can withstand large strains of between at least, for example, 10% and 20% (e.g., between at least 10% to 15%, 15% to 20%) without resulting in damage to the wetness sensing device 200.

In the wetness sensing device 200, the cover 202, the insulating portion 204, and the first and second conductive portions 206, 208 form the compressible and flexible portion. The cover 202, the insulating portion 204, and the first and the second conductive portions 206, 208 can be formed of materials and into geometries that allow them to be flexible and compressible. The cover 202, the insulative portion 204, and the first and second conductive portions 206, 208 can each have a low modulus of elasticity that is between, for example, 0.1 MPa to 100 MPa (e.g., 0.01 MPa to 1 MPa, 1 MPa to 10 MPa, or 10 MPa to 20 MPa). In some cases, the cover 202, the insulative portion 204, and the first and second conductive portions 206, 208 are formed of elastomers, such as, for example, ethylene propylene diene monomer (EPDM) rubber, fluorocarbon rubber, silicone rubber, fluorosilicone rubber, polyether block amides, Chloropene rubber, Butyl rubber, among other elastomeric materials.

The cover 202, the insulative portion 204, and the first and second conductive portions 206, 208 can also be formed using a foam molding process that forms foam elastomeric material. The foam elastomeric material can be a closed cell foam. The wetness sensing device 200 can include foam material between the inner surface 222 and the outer surface 221 in the form of the cover 202, the insulative portion 204, and the conductive portions 206, 208. The foam elastomeric material includes air voids such that forces on the wetness sensing device 200 initially cause the material to collapse into the air voids before the modulus of elasticity of the elastomeric material governs the stress-strain response of the wetness sensing device 200. The foam elastomeric material allows the wetness sensing device 200 to be compressible and thus easily conformable to the skin. The compressibility, conformability, and flexibility enable the inner surface 222 to be pressed against the skin to conform to the geometries of the venous access site.

Due to the foam elastomeric material, in response to a compressive stress, the wetness sensing device 200 can exhibit a nonlinear stress-strain response curve. The stress-strain response curve of the wetness sensing device 200 can include a portion where the collapse of the foam governs (e.g., when the wetness sensing device 200 is first compressed) and a subsequent portion where the modulus of elasticity governs (e.g., when the wetness sensing device 200 is compressed past the point when the foam collapses). Before the portion when the collapse of the foam governs, the stiffness can be initially high due to initial loads require to cause buckling of cell structures of the foam. After the cell structures begin to buckle, the collapse of the foam governs, resulting in lower stiffnesses. The cell size for the foam structure can have a width between 0.2 mm and 2 mm. At lower compressive stresses, the compressive stresses cause the foam to collapse, resulting in high compressive strain and thus a low stiffness. At higher compressive stresses, as more of the cell structures in the foam buckle, the modulus of elasticity of the foam elastomeric material governs, resulting in low compressive strain and thus a high stiffness as compared to the low stiffness when the foam first collapses.

Additionally, the foam elastomeric material can have a density of, for example, 0.01 to 1 gram per cubic centimeter (e.g., 0.01 to 0.1 grams per cubic centimeter, 0.1 to 0.5 grams per cubic centimeter, or 0.5 grams to 1 gram per cubic centimeter). The cover 202, the insulative portion 204, and the first and second conductive portions 206, 208 can have a durometer of, for example, 20 shore A and 80 shore A.

The material and structural properties of each of the cover 202, the insulating portion 204, and the first and second conductive portions 206, 208 allow these components to be flexible and compressible and thus conform to the skin of the wearer, such as, for example, the skin around the forearm of the wearer. The compressibility of the wetness sensing device 200 causes the wetness sensing device 200 to easily conform to geometries against which the inner surface 222 of the wetness sensing device 200 is pressed. During use of the wetness sensing device 200 on the skin of the wearer, the compressibility of the wetness sensing device 200 can prevent an operator from inadvertently placing excessive pressure on the wetness sensing device 200. As a result, application of the wetness sensing device to the skin of wearer is less likely to result in discomfort due to, for example, impingement of the skin and movement of the venous needle.

The first and second conductive portions 206, 208 are exposed along the inner surface 222 of the wetness sensing device 200 (e.g., a surface applied to skin of the wearer of the wetness sensing device 200). Similarly, the insulative portion 204 is also exposed along the inner surface 222. Blood that leaks from the wearer contacts the inner surface 222 and thus contacts the first and second conductive portions 206, 208 and the insulative portion 204. The first and second conductive portions 206, 208 can directly contact the skin of the wearer of the medical wetness sensing device 200 when the wetness sensing device 200 is worn by the wearer. Because the insulative portion 204 and the first and second conductive portions 206, 208 are compressible, they can easily conform to the skin of the wearer and thus can closely contact any blood that leaks from the patient. As a result, the first and second conductive portions 206, 208 can be in direct fluid communication with blood that, for example, leaks from a venous access site of the wearer.

The insulative portion 204 separates the first conductive portion 206 from the second conductive portion 208 and is electrically insulative. The first and second conductive portions 206, 208 define a gap 224 that is filled, in part, by the electrically insulative portion 204. The gap 224 can have a width between, for example, 0.5 to millimeters to 4 millimeters (e.g., 0.5 millimeters and 1 millimeter, 1 millimeter and 2 millimeters, or 2 millimeters and 4 millimeters). As a result, the insulative portion 204 electrically isolates the first and second conductive portions 206, 208 from one another.

The first and the second conductive portions 206, 208 are electrically conductive. In some examples, the first and second conductive portions 206, 208 are composited with black carbon, graphene flakes, carbon nanotubes, silver, nickel, silver-coated fibers, metal fibers, metal mesh, or other conductive materials that allow the first and conductive portions 206, 208 to be conductive. Additionally or alternatively, the first and the second conductive portions 206, 208 can include electrically conductive ink (e.g., metal oxide inks, metallic inks), copper wires, and other electrically conductive paths along the inner surface 222. In some cases, the first and second conductive portions 206, 208 can be laminated with a conductive coating. The coating can include conductive metal fillers such as, for example, nickel-copper alloys and silver-aluminum alloy. The coating can be formed of a metalized fiber mesh that can conduct electricity.

The foam elastomeric material can provide sufficient porosity to the insulative portion 204 and the first and second conductive portions 206, 208 such that blood (e.g., from a blood leak) can infiltrate into the insulative portion 204 and provide an electrical path through the insulative portion 204. Because the blood includes salts, the blood is electrically conductive. When the insulative portion 204 comes into contact with the blood, the blood can create the electrical path through the insulative portion 204. Because the insulative portion 204 separates the first and second conductive portions 206, 208, presence of blood, which forms the electrical path, electrically connects the first conductive portion 206 with the second conductive portion 208.

The printed circuit board 212 can include appropriate electrical components to control operations of the printed circuit board 212 described herein. The printed circuit board 212 can include, for example, a microcontroller to process, generate, transmit, and receive electrical signals.

The printed circuit board 212 can detect electrical continuity between the first and second conductive portions 206, 208 by transmitting electrical test signals through the first and second conductive portions 206, 208. For example, the printed circuit board 212 can transmit the test signals through one of the first and second conductive portions 206, 208 and determine whether the test signals propagate through the other conductive portion.

The first and second conductive portions 206, 208 are each electrically connected to the contact pad 210, which electrically connects the first and second conductive portions 206, 208 to the printed circuit board 212. The contact pad 210 can include electrical traces that connect each of the conductive portions 206, 208 to the printed circuit board 212 while keeping the conductive portions 206, 208 electrically isolated from one another.

In the absence of blood, the printed circuit board 212 can detect that the first and second conductive portions 206, 208 do not form a closed electrical loop. In the presence of blood, the printed circuit board 212 can detect that the first and second conductive portions 206, 208 form a closed electrical loop (e.g., are electrically continuous). In the presence of the blood, the electrical test signal transmitted through the first and second conductive portions 206, 208 indicate electrical continuity between the first electrically conductive portion 206 and the second electrically conductive portion 208.

The printed circuit board 212 can determine that an electrical resistance below a predetermined threshold indicates that the first and second conductive portions 206, 208 form the closed electrical loop or are electrically continuous. Electrical resistances below a threshold between, for example, 500 Kohms and 1 Mohm can indicate electrical continuity between the first and second conductive portions that could occur in the presence of blood.

In response to detecting electrical continuity through the first and second conductive portions 206, 208, the printed circuit board 212 can generate an electrical signal indicating the presence of blood along the inner surface 222. Similarly, in response to detecting electrical isolation between the first and second conductive portions 206, 208 (e.g., the first and second conductive portions 206, 208 are not electrically connected), the printed circuit board 212 can generate an electrical signal indicating the absence of blood along the inner surface 222. In some cases, in response to detecting the electrical isolation, the printed circuit board 212 can simply not transmit an electrical signal. The first and second conductive portions 206, 208 are thus configured to cause the printed circuit board 212 to generate a signal indicating the absence or presence of a liquid (e.g., blood) on the inner surface 222.

The printed circuit board 212 can transmit the electrical signal to a wireless transceiver 226, which can, based on the electrical signal, generate a wireless signal indicating the absence of blood or the presence of blood. The printed circuit board 212 and the wireless transceiver 226 are embedded beneath the outer surface 221 of the wetness sensing device 200. The wireless signal can be transmitted to a wireless transceiver of an extracorporeal system, a dialysis machine, or other treatment device (e.g., the wireless transceiver 118 of FIG. 1). The wireless transceiver 226 can transmit the wireless signal until the wireless transceiver receives a wireless stop signal including instructions to stop transmitting the wireless signal. For example, the treatment device can transmit a wireless stop signal to the wireless transceiver 226 after, for example, the blood leak causing the presence of the blood has been resolved.

The printed circuit board 212 receives power from the power source 214 to execute various electrical operations. The printed circuit board 212 can use the power to transmit the test signals to detect an absence or presence of electrical continuity that can be caused by the absence or presence of blood (or other conductive solution) in the insulative portion 204. The power source 214 further provides the power to energize the wireless transceiver 226 so that the wireless transceiver 226 can receive the electrical signal from the printed circuit board 212 and can generate and transmit the wireless signal.

While in the absence of blood, the wetness sensing device 200 can operate in an idle state in which the printed circuit board 212 transmits the electrical test signals without generating the electrical signal and the wireless signal. The idle state has a reduced power requirement, as the printed circuit board 212 does not operate the wireless transceiver during the idle state.

Figure 5:
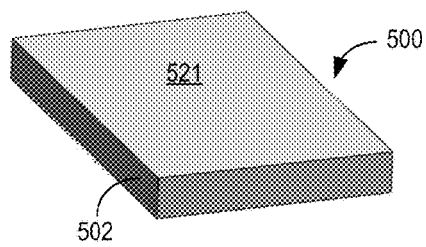
FIG. 5 is a top perspective view of another example of a wetness sensing device.
Figure 6:
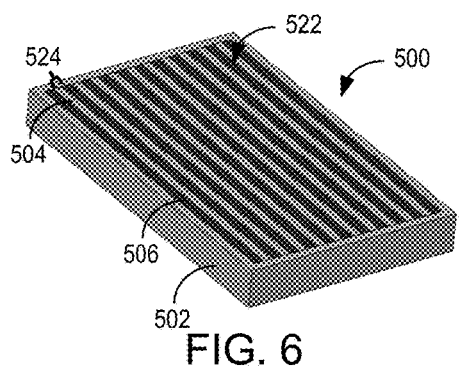
FIG. 6 is a bottom perspective view of the wetness sensing device of FIG. 5.

The wetness sensing device 200 of the first example has been described to have interlocking conductive portions 206, 208 separated by the insulative portion 204. Additionally, the conductive portions 206, 208, the insulative portion 204, and the cover 202 have been described to be made of foam elastomeric material to bestow compressibility and flexibility properties to those parts. Alternatively or additionally, the insulative and conductive portions of the wetness sensing device can be made of separate compressible tubing that allows the insulative and conductive portions to be compressible and flexible. Referring to FIGS. 5 to 7, which depicts a second example of the wetness sensing device, a wetness sensing device 500 includes a cover 502 housing an insulative portion 504 and conductive portions 506. The cover 502 further houses a contact pad 510, and an electrical system 513. The wetness sensing device 500 differs from the wetness sensing device 200 in that the structure of the conductive portions 506 and the insulative portion 504 differ from the structure of the conductive portions 206, 208 and the insulative portion 204.

As in the first example, the cover 502 can further include a power source cover (e.g., the power source cover 220 of FIGS. 2 to 5), and the cover 502 and the power source cover can define an outer surface 521 that is generally not exposed to blood leaking from a wearer of the wetness sensing device 500.

The wetness sensing device 500 includes a compressible and flexible portion that can experience large deformations in response to compression, thus allowing the inner surface 522 of the wetness sensing device 500 to conform to the skin of the wearer. The compressible and flexible portion achieves similar properties and advantages as described with respect to the compressible and flexible portion of the wetness sensing device 200. In the case of the wetness sensing device 500, the cover 502, the insulating portion 504, and the conductive portions 506 form the compressible and flexible portion. The cover 502, the insulating portion 504, and the conductive portions 506 can be formed of materials and into geometries that allow them to be flexible and compressible and thus conformable to skin of the wearer. The cover 502, the insulating portion 504, and the conductive portions 506 can be formed of similar materials as those used for the cover 202, the insulative portions 204, and the conductive portions 206, 208 of the wetness sensing device 200, such as, for example, the elastomers described herein and materials having the moduli of elasticity described herein.

The insulative portions 504, and the conductive portions 506 can be formed into compressible tubes that provide a nonlinear stress-strain curve. The compressible tubes define an inner cavity 515. Forces and stresses in a direction from the outer surface 521 toward an inner surface 522 thus cause the compressible tubes to collapse before the modulus of elasticity of the material of the insulative portions 504 and the conductive portions 506 governs the stress-strain response. The wetness sensing device 500, by including the compressible and collapsible tubes, can achieve compressibility similar to the compressibility described for the wetness sensing device 200.

Due to the inner cavity 515 of the insulative portion 504 and the conductive portions 506, in response to a compressive stress, the wetness sensing device 200 exhibits the nonlinear stress-strain response. The stress-strain response curve of the wetness sensing device 500 can include a portion where the collapse governs and a subsequent portion where the modulus of elasticity governs. At lower compressive stresses, the compressive stresses cause the compressible tubes to collapse, resulting in high compressive strain and thus a low stiffness. At higher compressive stresses, the modulus of elasticity of the elastomeric material governs, resulting in low compressive strain and thus a high stiffness as compared to the low stiffness when the tube first collapses.

In an uncompressed state, the compressible tubing can have a density of, for example, 0.3 to 5 grams per cubic centimeter (e.g., 0.3 to 1 gram per cubic centimeter, 1 to 3 grams per cubic centimeter, and 3 to 5 grams per cubic centimeter). The cover 502, the insulative portion 504, and the conductive portions 506 can have a durometer of, for example, 20 shore A and 80 shore A. The compressibility and flexibility of each of the cover 502, the insulating portion 504, and the conductive portions 506 allows the wetness sensing device 500 to conform to the skin of the wearer, and, in particular, enables the inner surface 522 of the wetness sensing device 500 to maintain close contact with and conform to the skin of the wearer.

The conductive portions 506 are exposed along the inner surface 522 of the wetness sensing device 500 (e.g., a surface applied to skin of the wearer of the wetness sensing device 500). Similarly, the insulative portion 504 is also exposed along the inner surface 522. Blood that leaks from the wearer contacts the inner surface 522 and thus contacts the conductive portions 506 and the insulative portion 504. Because the insulative portions 504 and the conductive portions 506 are compressible, they can easily conform to the skin of the wearer.

The conductive portions 506 can directly contact the skin of the wearer of the medical wetness sensing device 500 when the wetness sensing device 500 is worn by the wearer. Blood leaking from the wearer can easily contact the conductive portions 506 and the insulative portions 504.

Each of the insulative portions 504 separates the conductive portions 506 from one another to electrically isolate the conductive portions 506 from one another. The conductive portions 506 define gaps 524 that is filled, in part, by the electrically insulative portions 504. The gaps 524 each can have a width between, for example, 0.5 to millimeters to 4 millimeters (e.g., 0.5 millimeters and 1 millimeter, 1 millimeter and 2 millimeters, or 2 millimeters and 4 millimeters).

The conductive portions 506 can include materials and features similar to those described with respect to the first and second conductive portions 206, 208 so that the conductive portions 506 are electrically conductive.

Blood on the inner surface 522 can provide an electrical path along the inner surface 522 through the insulative portion 504. Because the blood includes salts, the blood is electrically conductive. Thus, when the insulative portion 504 comes into contact with the blood, the blood can create the electrical path along the insulative portion 504. Because the insulative portion 504 separates the conductive portions 506, presence of blood can electrically connect the conductive portions 506 (e.g., connect two or more of the conductive portions 506).

The electrical system 513 can perform similar functions as those described with respect to the printed circuit board 212, the power source 214, and the wireless transceiver 226. The electrical system 513 can include a printed circuit board (e.g., the printed circuit board 212), a power source (e.g., the power source 214), and a wireless transceiver (e.g., the wireless transceiver 226). The electrical system 513 can further generate electrical test signals, electrical signals, and wireless signals as described herein. As in the wetness sensing device 200, the power source of the electrical system 513 provides power to the electrical system 513 to perform the functions as described herein. The power source can also be removable through the power source cover.

The conductive portions 506 are each electrically isolated from one another and thus conduct electrical test signals generated by the electrical system 513. The electrical test signals, upon transmission through the conductive portions 506, can indicate an absence or presence of blood along the inner surface 522. In the absence of blood, the electrical test signals indicate the absence of blood when the conductive portions 506 are electrically isolated from one another. In the presence of blood, the electrical test signals indicate the presence of blood when a continuous electrical path exists between two or more of the conductive portions 506 due to, for example, blood serving as an electrical path across the insulative portion 504.

The electrical system 513 can detect electrical continuity (indicated by, e.g., a resistance along an electrical path below a threshold resistance) between the conductive portions 506 by transmitting electrical test signals through the conductive portions 506. The conductive portions 506 are each electrically connected to the contact pad 510, which electrically connects the conductive portions 506 to the electrical system 513. The contact pad 510 does not electrically connect the conductive portions 506 to one another. In the absence of blood, the electrical system 513 can detect that the conductive portions 506 do not form a closed electrical loop or are electrically discontinuous. In the presence of blood, the printed circuit board can detect that two or more of the conductive portions 506 form a closed electrical loop (e.g., are electrically continuous). In the presence of the blood, the electrical test signals conducted through the first and second conductive portions 206, 208 indicate electrical continuity between the first electrically conductive portion 206 and the second electrically conductive portion 208.

In response to detecting electrical continuity through the conductive portions 506, the electrical system 513 can generate an electrical signal indicating the presence of blood along the inner surface 522. Similarly, in response to detecting electrical isolation between the first and second conductive portions 506 (e.g., the first and second conductive portions 206, 208 are not electrically connected), the electrical system 513 can generate an electrical signal indicating the absence of blood along the inner surface 522. The conductive portions 506 are thus configured to cause the electrical system 513 to generate a signal indicating the absence or presence of blood on the inner surface 222.

The electrical system 513 can, based on the electrical signal, generate a wireless signal indicating the absence of blood or the presence of blood. As described herein, the wireless signal can be transmitted to an extracorporeal system, a dialysis machine, or other treatment device (e.g., the wireless transceiver 118 of FIG. 1).

While the insulative portions (e.g., the insulative portion 204, the insulative portion 504) have been described to fill gaps between the conductive portions (e.g., the conductive portions 206, 208 and the conductive portions 506), in some implementations, the conductive portions can be arranged along a surface of the insulative portion. In the third example, as shown in FIGS. 8, 9A, and 9B, a wetness sensing device 800 can include a cover 802 and an insulative portion 804 supporting conductive portions 806 along an inner surface 822 of the wetness sensing device 800. The conductive portions 806 are disposed along an inner surface 822 of the wetness sensing device 800. The cover 802 further houses a contact pad 810, and an electrical system 813. The wetness sensing device 800 differs from the wetness sensing device 200 and the wetness sensing device 500 in that the conductive portions 806 are not compressible.

The wetness sensing device 800 includes a compressible and flexible portion that can experience large deformations in response to compressive forces, thus allowing the wetness sensing device 800 and the inner surface 822 of the wetness sensing device 800 to conform to the skin of the wearer. The compressible and flexible portion achieves similar properties and advantages as described with respect to the compressible and flexible portion of the wetness sensing device 200. In the case of the wetness sensing device 800, while the conductive portions 806 may not be compressible, the insulative portion 804, which is compressible, can govern the structural characteristics of the wetness sensing device 800 so that the overall structure of the wetness sensing device 800 is compressible and flexible and so that the inner surface 822 of the wetness sensing device 800 can conform to the skin and the venous access site. The insulative portion 804 can thus form the compressible and flexible portion of the wetness sensing device 800. As a result, the wetness sensing device 800 can conform to skin of a wearer of the wetness sensing device 800 and the venous access site.

As in the first example, the cover 802 can further include a power source cover (e.g., the power source cover 220 of FIGS. 2 to 5), and the cover 802 and the power source cover can define an outer surface 821 that is generally not exposed to blood leaking from the wearer of the wetness sensing device 800.

The wetness sensing device 800 is flexible and compressible and thus conformable to the skin of the wearer, as described with respect to the wetness sensing device 200 and the wetness sensing device 500. The insulative portion 804 can be formed a foam elastomeric material as described with respect to, for example, the insulative portion 204 of the wetness sensing device 200. The insulative portion 804 can allow the wetness sensing device 800 to have a non-linear stress-strain response as described herein with respect to the wetness sensing device 200. The wetness sensing device 800, by including the foam elastomeric material, can achieve compressibility similar to the compressibility described for the wetness sensing device 200.

The conductive portions 806 of the wetness sensing device 800 can be formed of a flexible conductive ink that deforms with the insulative portion 804. For example, the conductive portions 806 can be formed using an inkjet or aerosol ink deposition process along the surface of the insulative portion 804. In some implementations, the conductive portions 806 can be flexible exposed copper wires that conduct electrical current.

While the conductive portions 806 may not be compressible, the conductive portions 806 make up a substantially smaller percent of the overall structure of the wetness sensing device 800. For example, the conductive portion 806 can have a thickness between 10 and 1000 micrometers, and the insulative portions 804 can have a thickness between 1 and 15 millimeters. The ratio of the thickness of insulative portion 804 to the thickness of the conductive portion 806 can be between 2 and 100. As a result, the insulative portions 804 can govern the overall stiffness of the wetness sensing device 800.

The electrical system 813 can perform similar functions as those described with respect to the printed circuit board 212, the power source 214, and the wireless transceiver 226. The electrical system 813 can include a printed circuit board (e.g., the printed circuit board 212), a power source (e.g., the power source 214), and a wireless transceiver (e.g., the wireless transceiver 226). The electrical system 813 can further generate electrical test signals, electrical signals, and wireless signals as described herein. As in the wetness sensing device 200, the power source of the electrical system 813 provides power to the electrical system 813 to perform the functions as described herein. The power source can also be removable through the power source cover.

Similar to the conductive portions 506, the conductive portions 806 are each electrically isolated from one another and thus conduct electrical test signals generated by the electrical system 813. The electrical test signals can indicate an absence or presence of blood along the inner surface 822. In the absence of blood, the electrical test signals indicate the absence of blood when the conductive portions 806 are electrically isolated from one another. In the presence of blood, the electrical test signals indicate the presence of blood when a continuous electrical path exists between two or more of the conductive portions 806 due to, for example, blood serving as an electrical path across the insulative portion 804.

While the conductive portions 806 have been described as formed from conductive ink, in some cases, the conductive portions can be fabric or cloth that includes conductive portions. In the fourth example of a wetness sensing device 1000 as shown in FIGS. 10A to 10C, a sheet of cloth 1001 includes polyethylene terephthalate (PET) fiber portions 1002 interwoven with stainless steel threads 1003. The sheet of cloth 1001 wraps around an insulative portion 1004 and includes insulative portions 1005 separated by conductive portions 1006. The cloth 1001 is attached to the insulative portion 1004 using, for example, adhesives or thermal bonding. The stainless steel threads 1003 form the conductive portions 1006, while the PET fiber portions 1002 form the insulative portions 1004. The cloth 1001 and the stainless steel threads 1003 form an inner surface 1022 of the wetness sensing device 1000.

The cloth 1001 enables the inner surface of the wetness sensing device 1000 to closely contact the skin of the wearer without being uncomfortable for the wearer. The cloth 1001 is soft and can improve comfort for the wearer of the wetness sensing device 1000. The cloth 1001 is also locally deformable such that the surface of the cloth 1001 can easily conform to the skin of the wearer. In some example, the cloth 1001 can be absorptive such that it absorbs any blood or liquid with which it comes into contact.

The stainless steel threads 1003 can form a mesh that extends along the inner surface of the wetness sensing device 800. One portion of the mesh can form a conductive portion separate from another conductive portion. The other conductive portion can be formed of a separate mesh of stainless steel threads.

The insulative portion 1004 is compressible. It can be formed of a foam elastomeric material as described with respect to, for example, the insulative portion 204 of the wetness sensing device 200. The insulative portion 1004 in cooperation with the cloth 1001 and the stainless steel threads 1003, which are highly flexible, enable the inner surface 1022 of the wetness sensing device 1000 to conform to the varying geometries of the venous access site.

The conductive portions 1006 conduct electrical test signals generated by the electrical system 1013. Similar to the conductive portions 806, the conductive portions 1006 are each electrically isolated from one another because each of the stainless steel threads 1003 are separated from one another. Because the PET fiber portions 1002 of the sheet of cloth 1001 can absorb blood and the stainless steel threads 1003 can conduct the electrical test signals, the electrical test signals can indicate an absence or presence of blood along the inner surface 1022 of the wetness sensing device 1000. In the absence of blood, the electrical test signals indicate the absence of blood when the conductive portions 1006 are electrically isolated from one another. In the presence of blood, the electrical test signals indicate the presence of blood when a continuous electrical path exists between two or more of the conductive portions 1006 due to, for example, blood serving as an electrical path across the insulative portion 1004.

The inner surfaces 222, 522, 822, 1022 of the wetness sensing devices 200, 500, 800, 1000, respectively, can each have areas appropriate for application on a venous access site (e.g., the venous access site 114). The areas can be between 10 and 20 square centimeters, 20 and 30 square centimeters, and 30 and 40 square centimeters. The wetness sensing devices 200, 500, 800, 1000 can have greater heights to increase the amount of compressive stress in which the low stiffnesses of, for example, the foam and the compressible tube collapsing govern. The height as measured from the inner surface 222, 522, 822, 1022 to the outer surface 221, 521, 821, 1021 of the wetness sensing device 200, 500, 800, 1000 can be between, for example, 7 and 20 millimeters (between, e.g., 7 and 10 millimeters, 10 and 15 millimeters, and 15 and 20 millimeters).

Hemodialysis Systems

Figure 11:
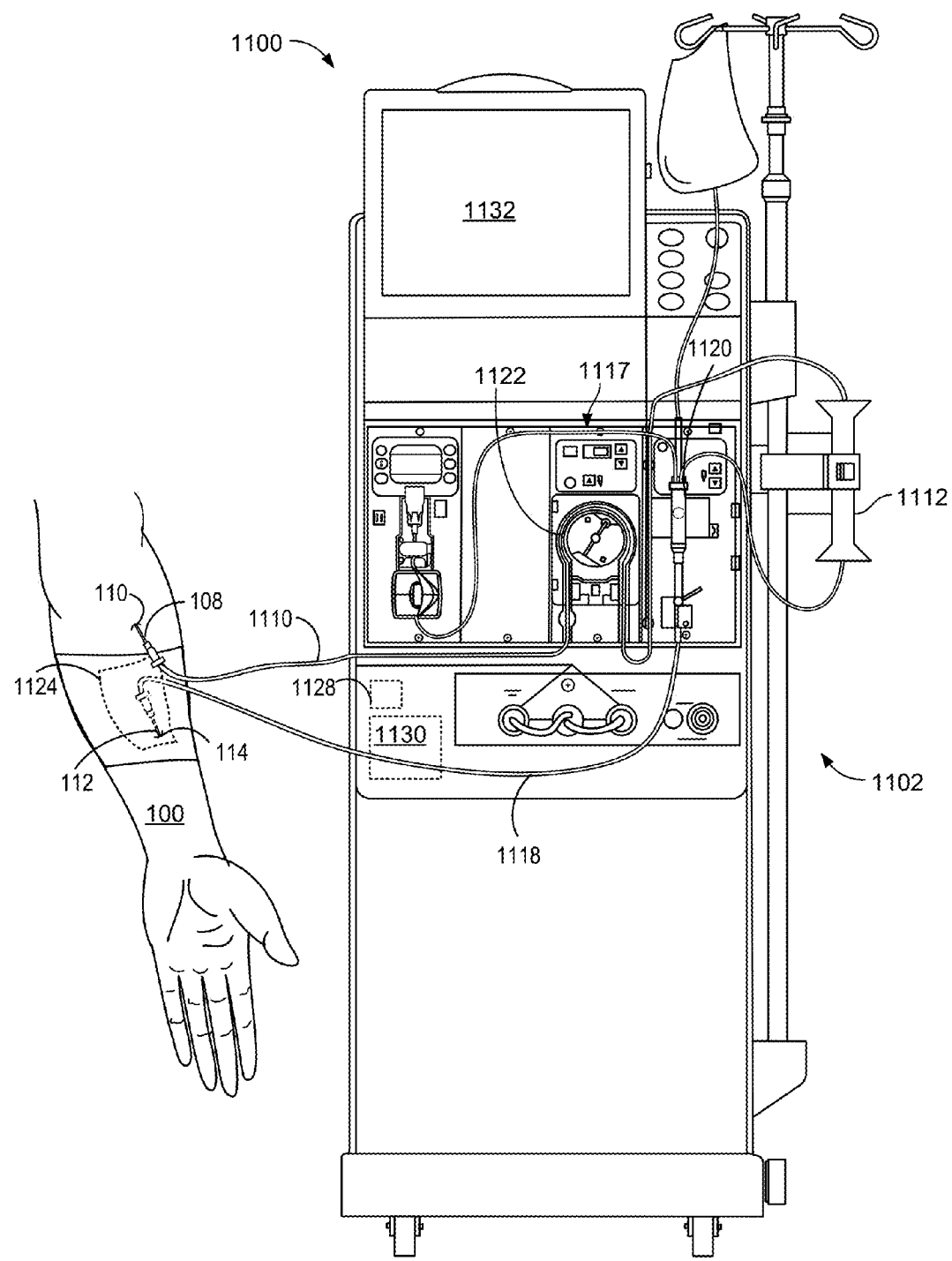
FIG. 11 is a front view of a hemodialysis system.

The wetness sensing devices described herein (e.g., the wetness sensing device 200, the wetness sensing device 500, and the wetness sensing device 800) can be used with hemodialysis systems. As shown in FIG. 11, a hemodialysis system 1100 includes a hemodialysis machine 1102 connected to the patient 100.

The arterial needle 108 inserted into the arterial access site 110 on the patient 100 connects the circulatory system of the patient 100 to the hemodialysis machine 1102 to allow blood from the patient 100 to flow through an arterial line 1110 to a dialyzer 1112 of the hemodialysis machine 1102. Dialysis solution (e.g., dialysate, salt solution) flows alongside the blood flowing through the dialyzer 1112 to filter the blood. The venous needle 112 inserted into the venous access site 114 connects the dialyzer 1112 to the circulatory system of the patient 100 to allow filtered blood to flow from the dialyzer 1112 through a venous line set 1117. The venous line set 1117 includes a venous line 1118 to conduct the filtered blood toward the patient and a drip chamber 1120 to remove, for example, air, debris, clots, and other particulate matter from the filtered blood. A peristaltic pump 1122 compresses portions of the arterial line 1110 to generate a flow of the filtered blood through the arterial line 1110 and the venous line set 1117 so that blood can be circulated throughout the hemodialysis system 1100.

A wetness sensing device 1124 (which can be any of the wetness sensing devices described herein, e.g., the wetness sensing devices 200, 500, and 800) applied on the patient 100 in the vicinity of the venous access site 114 on top of the venous needle 112 detects blood leaks from the venous access site 114. In an absence of liquid contacting an inner surface of the wetness sensing device 1124 (e.g., blood), the wetness sensing device 1124 can operate in an idle state. In the idle state, a power source (e.g., the power source 120, the power source 214) can supply power to a circuit (e.g., the printed circuit board 212, the electrical system 513) of the wetness sensing device 1124 to generate electrical test signals that can detect a presence of blood. The electrical test signals may not indicate the presence of blood, and the wetness sensing device 1124 can continue to periodically generate the electrical test signals to detect absence/presence of the blood.

When the electrical test signals indicate the presence of blood, the wetness sensing device 1124 can communicate with the hemodialysis machine 1102 to indicate to the hemodialysis machine 1102 that a blood leak has occurred. The wetness sensing device 1124 can include a wireless transceiver (e.g., the wireless transceiver 115) that can transmit a wireless signal that a wireless transceiver 1128 of the hemodialysis machine 1102 can receive. The wireless signal can indicate that the wetness sensing device 1124 has detected a presence of blood due to, e.g., blood leaking around the venous access site 114 from the venous needle 112. The wireless transceiver 1128 can generate electrical signals in response to receiving the wireless signal.

A controller 1130 of the hemodialysis machine 1102 can receive and transmit electrical signals operable to and from systems of the hemodialysis machine 1102. For example, the controller 1130 can receive electrical signals from the wireless transceiver 1128. The electrical signals can indicate that the wetness sensing device 1124 has detected the presence of blood. Based on the electrical signals, the controller 1130 can modify operations of components of the hemodialysis machine 1102, such as a pump speed of the peristaltic pump 1122, a display 1132 of the hemodialysis machine 1102, and other electrical and electromechanical systems.

Figure 12:
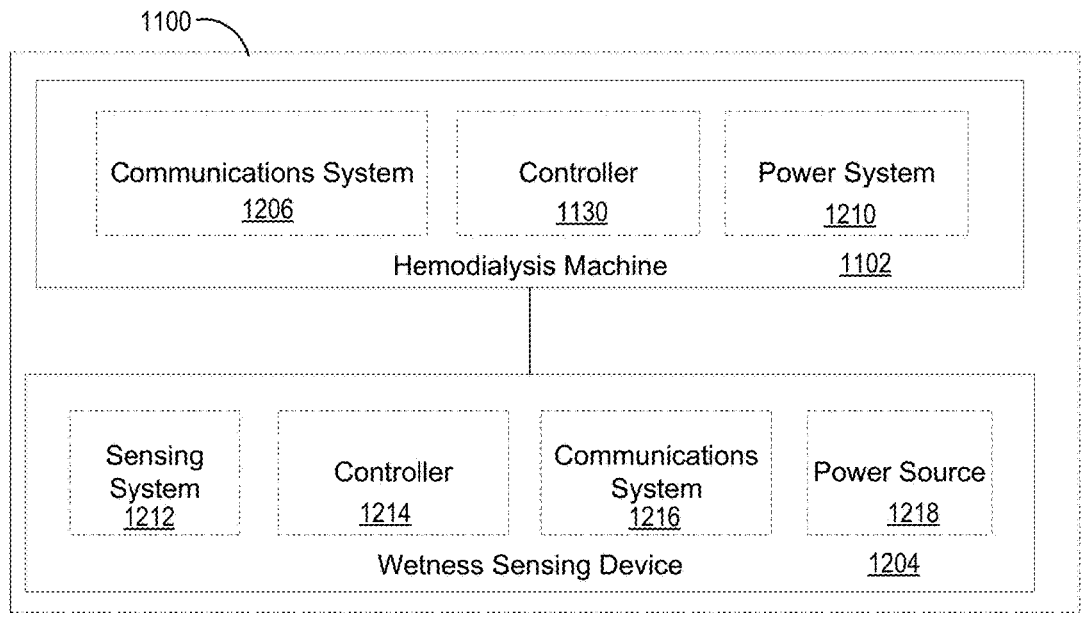
FIG. 12 is a block diagram of a hemodialysis system.

FIG. 12 schematically depicts the hemodialysis system 1100 including the hemodialysis machine 1102 and a wetness sensing device 1204. The hemodialysis machine 1102 includes a communications system 1206, the controller 1130, and a power system 1210. The wetness sensing device 1204 includes a sensing system 1212, a controller 1214, a communications system 1216, and a power source 1218.

The communications system 1206, 1216 can each include a wireless transceiver that enables both the hemodialysis machine 1102 and the wetness sensing device 1204 to transmit wireless signals to one another. The communications system 1206, 1216 can generate the wireless signals in response to receiving electrical signals. In some cases, the communications system 1206 of the hemodialysis machine 1102 includes a wireless receiver, and the communications system 1216 of the wetness sensing device 1204 includes a wireless transmitter. In such examples, the wetness sensing device 1204 can transmit wireless signals to the hemodialysis machine 1102.

The controller 1214 of the wetness sensing device 1204 can transmit and receive electrical signals from other systems of the wetness sensing device 1204. The controller 1214 can receive power from the power source 1218. The controller 1214 can also operate the sensing system 1212. The sensing system 1212 can include electrically conductive portions that conduct electrical signals in a manner dependent on an absence/presence of liquid (e.g., blood). In some examples, the controller 1214 can generate electrical test signals to transmit through at least part of the sensing system 1212. The controller 1214 can receive the electrical test signals after the electrical test signals follow an electric path in the wetness sensing device 1204. In some cases, the received electrical test signals can indicate presence/absence of blood. The controller 1214 can then transmit an electrical signal to the communications system 1206 so that the communications system 1216 can generate a wireless signal that the communications system 1206 of the hemodialysis machine 1102 can receive.

The controller 1130 of the hemodialysis machine 1102 can control operations of the hemodialysis machine 1102 by communicating with systems of the hemodialysis machine 1102. The controller 1130 receives power from the power system 1210 and can also modulate an amount of power that the power system 1210 delivers to individual systems of the hemodialysis machine 1102.

The controller 1130 can receive electrical signals from the communications system 1216 and generate further instructions for other systems. For example, the communication system 1216 can generate an electrical signal in response to receiving a wireless signal indicating that the wetness sensing device 1204 has detected the presence of blood caused by a blood leak. Upon receiving the electrical signal, the controller 1130 can deliver electrical signals to a pump, a display, or other electrical system of the hemodialysis machine 1102. These electrical signals can modify operations of these electrical systems such that the blood leak can be resolved.

Methods of Use

Figure 13:
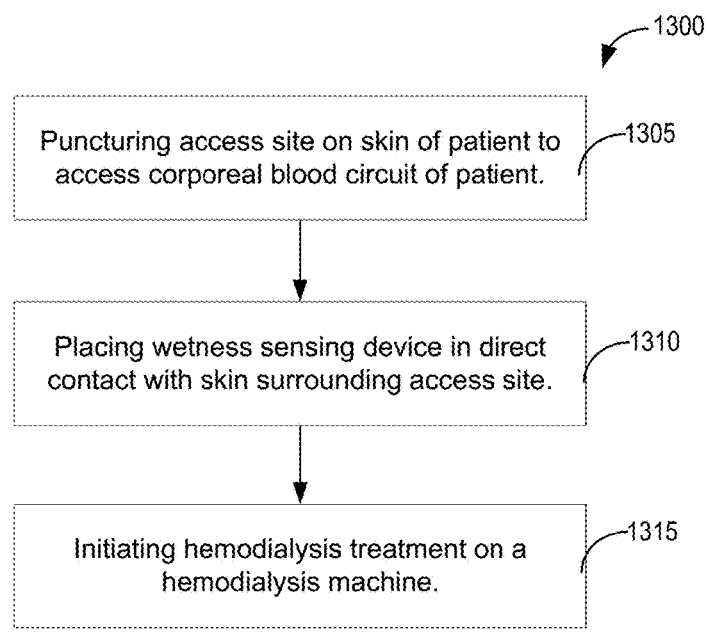
FIG. 13 is a flow chart of a method of using a wetness sensing device.

Shown in FIG. 13, a method 1300 of using a wetness sensing device (e.g., the wetness sensing device 200, the wetness sensing device 500, the wetness sensing device 800, or other wetness sensing device described herein) during a hemodialysis treatment of a patient is described herein.

At step 1305, an operator (e.g., a patient, a physician, a nurse, a medical practitioner) punctures an access site on skin of the patient to access a corporeal blood circuit of the patient. Before initiating the hemodialysis treatment, now also referring to FIG. 11, the operator can disinfect and clean skin of the patient 100 and then insert the arterial needle 108 into the arterial access site 110 and the venous needle 112 into the venous access site 114. The operator can thus use the arterial needle 108 and the venous needle 112 to puncture the respective access sites 110, 114 on the skin of the patient to access the circulatory system of the patient 100. The arterial needle 108 and the venous needle 112, when inserted, place the circulatory system of the patient 100 in fluid communication with the hemodialysis machine 1102.

At step 1310, the operator places a wetness sensing device in direct contact with the skin of the patient. As shown in FIG. 11, after inserting the arterial needle 108 and the venous needle 112, the operator can apply the wetness sensing device 1124 (e.g., the wetness sensing device 200, the wetness sensing device 500, the wetness sensing device 800, or other wetness sensing device described herein) to the skin of the patient 100 in the vicinity of the venous access site 114. The operator can place the wetness sensing device 1124 in direct contact with the skin surrounding the venous access site 114. In particular, the operator can firmly place the inner surface of the wetness sensing device against the venous access site 114 such that the inner surface conforms to the venous access site 114. The wetness sensing device 1124 can thus detect blood that leaks from the venous access site 114 in the event of, for example, dislodgement of the venous needle 112.

To secure the wetness sensing device 1124 to the skin surrounding the venous access site 114, the operator can apply an adhesive to the inner surface of the wetness sensing device 1124 and then place the inner surface on the skin of the patient 100 and above the venous needle 112. Additionally or alternatively, the operator can place a layer of gauze over the wetness sensing device 1124 and apply a medical tape or cloth around the gauze and the wetness sensing device 1124 to secure the wetness sensing device 1124 against the skin. The operator can wrap the cloth around an arm of the patient 100 such that the inner surface of the wetness sensing device 1124 is pressed against the venous access site 114, the skin of the patient 100, and the venous needle 112. The wetness sensing device 1124 can seal the inner surface of the wetness sensing device 1124 from an outside environment such that blood leaking from the venous access site 114 remains sealed between the inner surface and the skin of the patient 100.

As described herein, during use of the wetness sensing device 1124, the compressibility and flexibility of the wetness sensing device 1124 can prevent the operator from inadvertently placing excessive pressure on the wetness sensing device 1124. As a result, application of the wetness sensing device 1124 to the skin of patient 100 is less likely to result in discomfort due to, for example, impingement of the skin and movement of the venous needle 112. Rather, the wetness sensing device 1124 conforms to the skin and the venous needle 112, thus placing the wetness sensing device 1124 in direct contact with the skin and thus any blood that leaks from the patient 100. The compressibility and flexibility of the wetness sensing device 1124 improve conformability of the inner surface of the wetness sensing device 1124 to the venous access site, thus improving the reliability of the wetness sensing device 1124 to detect blood leaks.

At step 1315, the operator can initiate the hemodialysis treatment on the hemodialysis machine 1102. Before initiating the dialysis treatment, the operator can further set various dialysis treatment parameters of the hemodialysis machine 1102. When the operator initiates the hemodialysis treatment, the peristaltic pump 1122 of the hemodialysis machine 1102 can circulate the blood from the patient 100 through the dialyzer 1112 to clean and filter the blood. Blood can travel along the venous line set 1117 from the patient 100 through the arterial needle 108 to the dialyzer 1112. After the dialyzer 1112 filters the blood, filtered blood can exit the dialyzer 1112 and travels along the venous line set 1117 through the venous needle 112 back to the patient 100. Within the dialyzer 1112, alongside the flowing blood, a dialysis solution that can include salts, buffers, and/or acids can remove toxins from the blood.

During treatment, if a blood leak occurs around the venous access site 114, the blood can cause the wetness sensing device 1124 to generate a wireless signal in response to the presence of the blood, as described herein. The blood can contact an inner surface of the wetness sensing device 1124 and then generate an electrically conductive path that would otherwise not be present in the absence of the blood. The wireless transceiver 1128 of the hemodialysis machine 1102 can receive the wireless signal and transmit a corresponding electrical signal to the controller 1130 of the hemodialysis machine 1102. In response to the electrical signal, the controller 1130 can control various operations of the hemodialysis machine 1102. For example, the controller 1130 can adjust the pump speed of the peristaltic pump 1122, turn off the peristaltic pump 1122, activate an audible alarm through a speaker, and/or display an error message on the display 1132 of the hemodialysis machine.

In response to changes in operation of the hemodialysis machine 1102 (e.g., the alarm, the error message, and changes in operations of the peristaltic pump 1122), the operator can modify the course of treatment to resolve the blood leak. The operator can replace a component of the hemodialysis machine 1102, such as, for example, the venous needle 112, the wetness sensing device 1124, or the venous line set 1117. In some cases, dislodgement of the venous needle 112 may have caused the blood leak, and the operator can simply adjust how the venous needle 112 is inserted into the patient 100 (e.g., a depth of penetration of the venous needle 112, an angle of penetration of the venous needle 112).

In the absence of blood, a controller (disposed on, for example, the printed circuit board 212, the electrical system 513, the electrical system 813) may operate the wetness sensing device 1124 in an idle state in which the controller monitors the wetness sensing device 1124 to determine if the wetness sensing device 1124 is detecting a presence/absence of blood. For example, the controller can periodically transmit electrical test signals that determine whether a closed electrical loop has been formed between different conductive portions of the wetness sensing device 1124, as described herein.

After completion the hemodialysis treatment, the operator can remove and dispose of the wetness sensing device 1124. The operator can then disconnect the arterial needle 108 and the venous needle 112 from the patient 100 and dispose of the venous line set 1117.

Alternative Implementations

The examples described herein can be implemented in a variety of ways without departing from the scope of the specification.

The examples of using wetness sensing devices described with respect to FIGS. 11 and 13 are directed to a hemodialysis treatment, though, in other implementations, the wetness sensing devices can be used for other appropriate medical treatments. As described herein, the wetness sensing devices can be used for medical procedures requiring access to the circulatory of the patient. The wetness sensing devices can additionally be used to detect liquids other than blood. These liquids can be removed or introduced to a patient. For example, the wetness sensing devices can be used during a diabetes treatment and can detect presence of insulin. The wetness sensing devices can be used during intravenous fluid delivery to detect water, saline, or other solutions. The wetness sensing devices can be use during drug delivery and other appropriate treatments in which liquid is transferred to and from the patient.

The wetness sensing devices (e.g., the wetness sensing device 102) has been described to be placed above the venous access site (e.g., the venous access site 114). Additionally or alternatively, the wetness sensing devices can be placed on top an arterial access site to detect blood leaking as the blood travels away from the patient.

While the inner surface of the wetness sensing device 102 has been described to be placed directly against the skin of the patient, in some cases, the wetness sensing device 102 can be placed over gauze or other soft medical fabric. In the event of a blood leak from the patient, the gauze absorbs the blood, the wetness sensing device 102 detects the blood through the gauze. Even though the gauze and the wetness sensing device 102 are separate, the compressibility and flexibility of the wetness sensing device 102 allows the inner surface of the wetness sensing device 102 to conform to the deformations of the gauze as the gauze conforms to the skin. The inner surface of the wetness sensing device 102 is able to maintain contact with the gauze and thus easily detect any blood that leaks onto the gauze.

The wetness sensing device 102 is compressible and flexible but may include additional structural and material properties. In some implementations, the wetness sensing device 102 is resilient. The inner surface of the wetness sensing device 102 is applied to the skin and takes on the curvature of the skin. Upon removal of the wetness sensing device 102 from the skin, the wetness sensing device 102, due to its resilience, can be restored to its initial geometric configuration (e.g., substantially flat or planar). In some cases, the inner surface of the wetness sensing device has a lower durometer so that the inner surface is soft. A soft inner surface can improve comfort for the wearer of the wetness sensing device.

While the electrical path in the presence of blood is described as being formed through the insulative portions, in some cases, the presence of blood forms an electrical path across the insulative portions or along a surface of the insulative portions. The blood can remain on a surface of the insulative portions, and the electrical path formed between first and second conductive portions is thus along the surface of the insulative portions.

The wetness sensing device 200 includes the two interlocking conductive portions 206, 208; the wetness sensing device 500 includes three separated conductive portions 206; and the wetness sensing device 800 includes seventeen separated conductive portions. A wetness sensing device can include any number of conductive portions appropriate to detect liquid contacting an inner surface of the wetness sensing device. The wetness sensing device can include additional (e.g., more than seventeen separated conductive portions) if the wetness sensing device is to be used over a large area over skin of a patient. For wetness sensing devices of similar area to those described with respect to the wetness sensing devices 200, 500, 800, additional conductive portions can decrease the gap between the conductive portions, thus decreasing the length of the electrical path that the liquid creates to electrically connect separated conductive portions. As a result, the wetness sensing devices having additional conductive portions may detect smaller amounts of liquid.

The printed circuit board 212 and the electrical systems 513, 813 determine whether continuity exists between separated conductive portions 206, 208, 506, 806 to detect presence of liquid on the inner surface of the wetness sensing device 200, 500, 800. Electricity continuity has been described to be indicated by a resistance below a threshold resistance for the electrical path that the electrical test signal takes along the conductive portions 206, 208, 506, 806. The threshold resistance can vary depending on the conductivities of the insulative portions and the conductive portions of various implementations of wetness sensing devices described herein.

In some examples, electrical systems of a wetness sensing device may detect changes in appropriate characteristics that can change in presence of liquid such as blood. The electrical systems may interpret a change in capacitance, current, voltage, or other appropriate electrical parameter as indicative of presence of liquid.

While the foam material of the insulative portions (e.g., the insulative portion 204, the insulative portion 504, and the insulative portion 804) has been described to absorb the blood to increase electrical conductivity of the insulative portion, in some examples, when the blood contacts the inner surface (e.g., the inner surface 222, the inner surface 522, and inner surface 822), the blood can remain on the inner surface. In these examples, the blood can conduct electrical current such that the test signals can conduct from one conductive portion to another conductive portion (e.g., the conductive portions 206, 208, the conductive portions 506, and the conductive portions 806).

While the modulus of elasticity of the insulative and conductive portions has been describe to be within particular ranges described herein, in some cases, the modulus of elasticity can be selected to match that of or be less than that of typical human skin. Similarly, other material properties, such as durometer and roughness, can be selected to match those or be less than those of human skin.

The wetness sensing devices 200, 500, 800, and 1000 have each been described to include a compressible and flexible portion that enables the wetness sensing device to conform to the skin of the wearer and compress in response to being placed against curved geometry underlying the wetness sensing device. In some cases, instead of being formed from foam material, the compressible and flexible portions can be formed from a solid or dense elastomeric material that can withstand large strains. For example, the insulative portions, the conductive portions, and/or the cover can be formed from the dense elastomeric material that enables the wetness sensing device to compress and conform to geometry underlying the wetness sensing device. In this regard, even as the wetness sensing device is placed on curved surfaces, such as a wearer's forearm or a venous needle, the dense elastomeric material can sufficiently withstand the large strains caused by bending about the curved surfaces so that the wetness sensing device maintains integrity and functionality during use.

Combinations of various materials and structures described herein can form the compressible and flexible portion of the wetness sensing device, and, in this regard, can enable the wetness sensing device to achieve compressibility similar to the compressibility described for the wetness sensing device 200. In some implementations, the insulative portions and the cover are compressible, while the conductive portions are flexible but not compressible. In some implementations, the insulative portions, the cover, and the conductive portions are all compressible.

The compressibility of the wetness sensing device 200, 500, 800, 1000 may further vary depending on the size of the patient's forearm. While the wetness sensing device 200, 500, 800, 1000 has been described to have a compressibility permitting strain between at least 10% and 20%, in some implementations, the amount of strain permitted may be greater or lower. For example, larger forearms that have a smaller curvature may require less compressibility and less strain, while smaller forearms that have a greater curvature may require more compressibility and more strain.

Patterns of the conductive portions 206, 208, 506, 806 along the inner surfaces of the wetness sensing devices 200, 500, 800, 1000 can be modified. The appropriate pattern to utilize may be determined based upon manufacturing characteristics such as cost and feasibility. In some cases, the wetness sensing devices include partitions that include separated sections that each independently detect liquid. The overall conductive pattern may comprise multiple sections each including conductive portions. The sections, in the presence and absence of blood alike, do not include an electrically continuous path therebetween. The sections and patterns may be arranged in any manner known in the art. For example, the inner surfaces of wetness sensing devices can be divided into quadrants, which can allow the wetness sensing devices to further determine a location, among four quadrants of the inner surface, where blood is detected.

The wetness sensing devices and the hemodialysis machine include wireless transceivers. In some cases, the wetness sensing devices can include wireless transmitters and the hemodialysis machine can include a wireless receiver. When the wetness sensing devices transmit wireless signals over the wireless transmitters, the microcontroller of the wetness sensing devices can disable transmission of the wireless signals after a predetermined period of time, such as, for example, 1 to 10 minutes.

Elements of different implementations described herein may be combined to form other implementations not specifically set forth above. Elements may be left out of the structures described herein without adversely affecting their operation. Furthermore, various separate elements may be combined into one or more individual elements to perform the functions described herein.

Various embodiments discussed herein may be combined with each other in appropriate combinations in connection with the system described herein. Additionally, in some instances, the order of steps in the flow chart (e.g., the flow chart of the method 1300) may be modified, where appropriate. Further, various aspects of the systems described herein may be implemented using software, hardware, a combination of software and hardware and/or other computer-implemented modules or devices having the described features and performing the described functions.

Software implementations of aspects of the system described herein may include executable code that is stored in a computer-readable medium and executed by one or more processors. The computer-readable medium may include volatile memory and/or non-volatile memory, and may include, for example, a computer hard drive, ROM, RAM, flash memory, portable computer storage media such as a CD-ROM, a DVD-ROM, a flash drive and/or other drive with, for example, a universal serial bus (USB) interface, and/or any other appropriate tangible or non-transitory computer-readable medium or computer memory on which executable code may be stored and executed by a processor. The system described herein may be used in connection with any appropriate operating system.

What is claimed is:

1. A medical wetness sensing device, comprising:
   a cover defining an outer surface;
   first and second electrically conductive portions housed in the cover and exposed along an inner surface of the medical wetness sensing device, the first and second electrically conductive portions being configured to transmit a test signal indicating an absence or presence of a liquid on the inner surface;
   an electrically insulative portion housed in the cover, the electrically insulative portion electrically isolating the first electrically conductive portion from the second electrically conductive portion; and
   a compressible portion that is flexible, compressible, and configured such that the inner surface of the medical wetness sensing device is conformable to skin of a wearer of the medical wetness sensing device, the compressible portion being formed by at least the first and second electrically conductive portions.

2. The medical wetness sensing device of claim 1, wherein the compressible portion comprises a foam elastomer.

3. The medical wetness sensing device of claim 2, wherein the foam elastomer has a density between 0.3 grams per cubic centimeter and 5 grams per cubic centimeter.

4. The medical wetness sensing device of claim 2, wherein:
   the electrically insulative portion comprises the foam elastomer and at least partially forms the compressible portion.

5. The medical wetness sensing device of claim 4, further comprising:
   a sheet of cloth forming the inner surface of the medical wetness sensing device, and
   a conductive mesh woven through the sheet of cloth such that the conductive mesh is exposed along the inner surface, the conductive mesh forming at least one of the first and second electrically conductive portions.

6. The medical wetness sensing device of claim 1, wherein the compressible portion comprises a compressible tube.

7. The medical wetness sensing device of claim 1, wherein the first and the second electrically conductive portions are disposed along a surface of the electrically insulative portion.

8. The medical wetness sensing device of claim 7, wherein the first and the second electrically conductive portions comprise a conductive ink deposited on the surface of the electrically insulative portion.

9. The medical wetness sensing device of claim 1, wherein the first and second electrically conductive portions define a gap therebetween, the gap being filled, in part, by the electrically insulative portion.

10. The medical wetness sensing device of claim 9, wherein the gap has a width between 0.5 and 4 millimeters.

11. The medical wetness sensing device of claim 1, wherein the first and second electrically conductive portions comprise at least one of black carbon, graphene flakes, carbon nanotubes, silver, copper, stainless steel mesh, and nickel.

12. The medical wetness sensing device of claim 1, wherein, in the presence of the liquid, the test signal transmitted by the first and second electrically conductive portions indicates electrical continuity between the first electrically conductive portion and the second electrically conductive portion.

13. The medical wetness sensing device of claim 1, further comprising a power source housed in the cover embedded beneath the outer surface of the medical wetness sensing device.

14. The medical wetness sensing device of claim 1, further comprising a wireless transmitter embedded beneath the outer surface of the medical wetness sensing device.

15. A hemodialysis system, comprising:
a hemodialysis machine; and
a medical wetness sensing device comprising:
a cover defining an outer surface,
a first and second electrically conductive portions housed in the cover and exposed along an inner surface of the medical wetness sensing device, the first and second electrically conductive portions being configured to transmit a test signal indicating an absence or presence of a liquid on the inner surface,
an electrically insulative portion housed in the cover, the electrically insulative portion electrically isolating the first electrically conductive portion from the second electrically conductive portion,
a compressible portion that is flexible, compressible, and configured such that the inner surface of the medical wetness sensing device is conformable to skin of a wearer of the medical wetness sensing device, the compressible portion formed by at least the first and second electrically conductive portions.

16. The medical wetness sensing device of claim 15, wherein, in the presence of the liquid, the test signal transmitted by the first and second electrically conductive portions indicates electrical continuity between the first electrically conductive portion and the second electrically conductive portion.

17. The medical wetness sensing device of claim 15, wherein the first and second electrically conductive portions define a gap therebetween, the gap being filled, in part, by the electrically insulative portion.

18. A method, comprising:
puncturing, using a needle, an access site on skin of a patient to access a corporeal blood circuit of the patient; and
placing a medical wetness sensing device over the skin surrounding the access site such that an inner surface of the medical wetness sensing device faces the skin, the medical wetness sensing device comprising:
a cover defining an outer surface;
a first and second electrically conductive portions housed in the cover and exposed along the inner surface of the medical wetness sensing device, the first and second electrically conductive portions being configured to transmit a test signal indicating an absence or presence of a liquid on the inner surface,
an electrically insulative portion housed in the cover, the electrically insulative portion electrically isolating the first electrically conductive portion from the second electrically conductive portion; and
a compressible portion that is flexible, compressible, and configured such that the inner surface of the medical wetness sensing device is conformable to the skin, the compressible portion being formed by at least the first and second electrically conductive portions.

19. The method of claim 18, further comprising securing the medical wetness sensing device to the skin with an adhesive.

20. The method of claim 18, further comprising securing the medical wetness sensing device to the skin with cloth wrapped around an arm of the patient.

21. The method of claim 18, further comprising initiating a hemodialysis treatment on a hemodialysis machine configured to receive a signal from the medical wetness sensing device, the signal indicating an absence or presence of a liquid on the inner surface of the medical wetness sensing device.

22. The method of claim 18, wherein placing the medical wetness sensing device in direct contact with the skin surrounding the needle further comprises placing the medical wetness sensing device in direct fluid communication with liquid that leaks from the access site.

23. The method of claim 18, wherein the compressible portion of the medical wetness sensing device is at least partially formed by the electrically insulative portion.

24. The method of claim 18, wherein the compressible portion of the medical wetness sensing device is at least partially formed by the cover.

25. The method of claim 21, wherein the signal is a wireless signal.

26. The medical wetness sensing device of claim 1, wherein the compressible portion is at least partially formed by the electrically insulative portion.

27. The medical wetness sensing device of claim 1, wherein the compressible portion is at least partially formed by the cover.

28. The medical wetness sensing device of claim 1, further comprising a wireless transmitter housed in the cover, the wireless transmitter being configured to transmit a wireless signal to a hemodialysis machine indicating the presence or absence of the liquid on the inner surface of the medical wetness sensing device.

29. The hemodialysis system of claim 15, wherein the compressible portion of the medical wetness sensing device is at least partially formed by the electrically insulative portion.

30. The hemodialysis system of claim 15, wherein the compressible portion of the medical wetness sensing device is at least partially formed by the cover.

31. The hemodialysis system of claim 15, wherein the medical wetness sensing device further comprises a wireless transmitter housed in the cover, the wireless transmitter being configured to transmit a wireless signal to a wireless receiver of the hemodialysis machine, the wireless signal indicating the presence or absence of the liquid on the inner surface of the medical wetness sensing device.

* * * * *

UNITED STATES PATENT AND TRADEMARK OFFICE
CERTIFICATE OF CORRECTION

PATENT NO. : 10,195,367 B2
APPLICATION NO. : 14/886427
DATED : February 5, 2019
INVENTOR(S) : Daniel Schmidt, Elliott Alber and Colin Weaver Page 1 of 1

It is certified that error appears in the above-identified patent and that said Letters Patent is hereby corrected as shown below:

On the Title Page

Item [57], Line 15, delete "device The" and insert --device. The--.

Signed and Sealed this
Second Day of April, 2019

Andrei Iancu
*Director of the United States Patent and Trademark Office*